(12) United States Patent
Mohl et al.

(10) Patent No.: US 8,177,722 B2
(45) Date of Patent: May 15, 2012

(54) METHOD AND DEVICE FOR THE INTERMITTENT OCCLUSION OF THE CORONARY SINUS

(75) Inventors: Werner Mohl, Altenmarkt/Thennenberg (AT); Ilinka Kajgana, Vienna (AT)

(73) Assignee: Miracor Medical Systems GmbH, Vienna (AT)

( * ) Notice: Subject to any disclaimer, the term of this patent is extended or adjusted under 35 U.S.C. 154(b) by 1041 days.

(21) Appl. No.: 11/629,401

(22) PCT Filed: Jun. 7, 2005

(86) PCT No.: PCT/AT2005/000203
§ 371 (c)(1),
(2), (4) Date: Aug. 16, 2007

(87) PCT Pub. No.: WO2005/120601
PCT Pub. Date: Dec. 22, 2005

(65) Prior Publication Data
US 2008/0119742 A1    May 22, 2008

(30) Foreign Application Priority Data
Jun. 14, 2004   (AT) ................. A 1012/2004

(51) Int. Cl.
*A61B 5/02*       (2006.01)
*A61M 29/00*   (2006.01)
(52) U.S. Cl. .............. 600/486; 600/485; 606/194

(58) Field of Classification Search .................. 600/485, 600/486; 606/194
See application file for complete search history.

(56) References Cited

U.S. PATENT DOCUMENTS
4,969,470 A * 11/1990 Mohl et al. ............... 600/486

FOREIGN PATENT DOCUMENTS
| AT | 410 396 | 9/2002 |
| EP | 0 230 996 | 8/1987 |
| WO | 03/008018 | 1/2003 |

OTHER PUBLICATIONS

International Search Report for PCT/AT2005/000203 mailed Aug. 24, 2005 (English and German).
Mohl, Werner et al. "Coronary Sinus Library, ICSO and PICSO" Society of Coronary Sinus Interventions, 2003. A. Holzhausens Nfg., Austria.

* cited by examiner

*Primary Examiner* — Patricia Mallari
*Assistant Examiner* — Christian Jang
(74) *Attorney, Agent, or Firm* — Fish & Richardson P.C.

(57) ABSTRACT

In a method for intermittently occluding the coronary sinus, in which in an alternating manner the coronary sinus is occluded by an occlusion device and the occlusion is released, the curve of the fluid pressure occurring in the coronary sinus after the release of the occlusion is estimated by calculation and the time of the beginning of the next occlusion is determined as a function of the estimated pressure curve.

21 Claims, 3 Drawing Sheets

METHOD AND DEVICE FOR THE INTERMITTENT OCCLUSION OF THE CORONARY SINUS

This application is the US national phase of international application PCT/AT2005/000203 filed 7 Jun. 2005, which designated the U.S. and claims benefit of AT A 1012/2004 filed 14 Jun. 2004, the entire contents of each of which are hereby incorporated by reference.

The invention relates to a method for intermittently occluding the coronary sinus, in which in an alternating manner the coronary sinus is occluded by an occlusion device and the occlusion is released, as well as a device for the intermittent occlusion of the coronary sinus.

Arterial blood, which supplies the heart muscle, is able to pass through healthy heart tissue while nourishing the same, yet has difficulty reaching ischemic tissue. As a result, the supply of ischemic tissue with nutrients and the discharge of metabolic catabolites from such ischemic tissue will be impaired.

In this context, it has already been proposed to supply ischemic tissue with blood through retrograde perfusion. This means that blood is tried to be allowed to flow back from the coronary sinus through the coronary venous system in counterflow by feeding blood from a different source into the coronary sinus, either by permanently connecting an artery with the coronary sinus or by temporarily inserting a catheter into the sinus, which catheter is supplied with blood taken from a remote artery and transported by the aid of a blood pump located outside the patient's body.

Another technique proposed for retroperfusion uses an inflatable balloon which is fixed to the end of a catheter to intermittently occlude the coronary sinus. The blood pressure in the coronary sinus rises during the occlusion at every heart beat so as to cause blood reaching the coronary sinus through the healthy tissue of the heart muscle to be flushed back into the ischemic tissue. For such an intermittent coronary sinus occlusion, the balloon end of the catheter is inserted either percutaneously or surgically. The other end of the catheter is supplied with a gas or fluid by a pump which causes the cyclic inflation and deflation of the balloon.

A typical application of blood retroinfusion in coronary veins through intermittent coronary sinus occlusion applies to myocardial protection during a short-term coronary arterial occlusion in the context of a cardiologic intervention. A typical such intervention comprises, for instance, the balloon dilatation of an arteriosclerotically constricted coronary artery. That method, which is also known as percutaneous transluminal coronary angioplasty (PTCA), comprises the conduction of a balloon catheter into the region of the coronary artery stenosis under X-ray control and the compression of the osclerotic plaque by the inflation of the balloon, which is located on the end of the catheter. During the dilatation of the balloon, no supply of the tissue with oxygen-containing blood takes place downstream in the artery with functional changes in the ischemic area of the myocard being detectable already at dilatations lasting longer than 30 seconds. Consequential problems of the ischemic protection of the myocard will also be faced with at other interventions aimed at coronary vascularization such as, e.g., atherectomy, coronary endoprostheses, laser applications and percutaneous valvular surgeries.

A device for the retroinfusion of coronary veins is, for instance, known from EP 230 996 A2, by which a pressure-controlled, intermittent coronary sinus occlusion can be performed. The device comprises a means for occluding the sinus such as, e.g., an inflatable balloon catheter, a pressure measuring unit for measuring the fluid pressure within the coronary sinus and a control unit which generates triggering signals for the occlusion device to trigger or release an occlusion. The control unit is devised in a manner that the pressure maximum in the coronary sinus is measured during every heart beat, a plateau value of the pressure maxima of consecutive heart beats is estimated by calculation and the occlusion of the coronary sinus is released on the basis of the plateau value of the pressure maxima.

The occlusion of the coronary sinus causes a pressure increase and, as a result, a retroperfusion of blood via the respective vein into the nutritive capillaries of the ischemic area so as to enable the supply of nutrients to that area. At a release of the occlusion, the retroperfused blood is flushed out with the metabolic waste products being carried off at the same time. In the method according to EP 230 996 A2, a systolic pressure curve is, thus, estimated based on the measurement of the pressure maximum in the coronary sinus during every heart beat, whereby the occlusion of the coronary sinus is released as a function of the plateau value of the systolic pressure curve.

In order to determine the time at which the occlusion is to be triggered again, an empirically acquired formula is proposed according to the method of EP 230 996 A2, which allows for an estimation of the interval between the end of the occlusion and the peak value of the reactive hyperemia. This empirically acquired formula is based on parameters of the systolic and diastolic pressure curves determined for the occluded coronary sinus, with a linear regression being performed subsequently. By the method according to EP 230 996 A2 it has become possible to retrigger the occlusion only after the occurrence of the peak value of the reactive hyperemia, i.e. after the impounded blood has streamed out of the coronary sinus. Yet, due to the inaccuracy of the empirically determined formula, the time until the next occlusion of the coronary sinus will occasionally be chosen too long for safety reasons, which means that it will be waited too long before triggering the next occlusion. That method has, thus, become inefficient, apart from the fact that the calculational implementation of the method has turned out to be cumbersome and not accomplishable at an adequate speed.

The present invention aims to propose a method and device for the intermittent occlusion of the coronary sinus, which provide an increased accuracy in the determination of the optimal time for the triggering of the next occlusion, while directly taking into account the pressure conditions prevailing in the non-occluded coronary sinus.

To solve this object, the method according to the invention essentially consists in that the curve of the fluid pressure occurring in the coronary sinus after the release of the occlusion is estimated by calculation and the time of the beginning of the next occlusion is determined as a function of the estimated pressure curve. The respective device according to the invention includes an occlusion device for the alternate occlusion of the coronary sinus and release of the occlusion as well as a control device for delivering control signals to the occlusion device to control the time of the beginning and release of the occlusion and is characterized in that the control device is connected with an arithmetic unit configured to calculationally estimate the curve of the fluid pressure occurring in the coronary sinus after the release of the occlusion, wherein the time of the beginning of the next occlusion is determined as a function of the estimated pressure curve. In accordance with the invention, the pressure conditions in the coronary sinus during the non-occluded phase (release phase) are, thus, immediately estimated to determine the time of the beginning of the next occlusion, and it is, therefore, no longer necessary to resort to empirically acquired formulae such that the accuracy of the method will be enhanced. The knowledge or prediction of the curve of the pressure prevailing in the coronary sinus during the release phase allows for direct conclusions as to various other parameters that are decisive for the method, such as, for instance, the flow volume and the peak value of the reactive hyperemia, and permits the precise control of the occlusion device.

A further refinement of the method according to a preferred embodiment is provided in that the pressure maxima occurring in the coronary sinus during consecutive heart beats after the release of the occlusion are estimated by calculation and the time of the beginning of the next occlusion is determined as a function of the estimated pressure maxima. It is feasible to proceed in a similar manner by replacing the pressure maxima with the pressure minima. For the realization of this preferred method, the configuration is further developed such that the arithmetic unit is configured to estimate the pressure maxima occurring in the coronary sinus during consecutive heart beats after the release of the occlusion, wherein the time of the beginning of the next occlusion is determined as a function of the estimated pressure maxima.

After the release of the occlusion, a relaxation process takes place in the coronary sinus, whereby the pressure curve can be approximated by an exponential function. According to a preferred mode of procedure, it is therefore contemplated that the pressure maxima occurring in the coronary sinus during consecutive heart beats after the release of the occlusion are approximated by an exponential function and the time of the beginning of the next occlusion is determined as a function of the plateau value of said exponential function. The respective device is further developed in a manner that the arithmetic unit is configured to approximate by an exponential function the pressure maxima occurring in the coronary sinus during consecutive heart beats after the release of the occlusion, wherein the time of the beginning of the next occlusion is determined as a function of the plateau value of said exponential function. In doing so, it may again be proceeded in an analogous manner for the approximation of the pressure minima. The exponential function connecting the pressure maxima or pressure minima and, hence, reflecting the systolic or diastolic pressure curve, respectively, asymptotically approaches a plateau value corresponding to the lowest pressure in the coronary sinus after the release of the occlusion or the starting pressure in the coronary sinus prior to the initiation of the intermittent occlusion, respectively. This plateau value is, therefore, particularly suitable for the determination of the occlusion intervals. According to a further preferred embodiment, it may, for instance, be proceeded in a manner that the occlusion of the coronary sinus is released as the exponential function reaches a defined multiple of the forecast plateau value. In this case, the release phase is terminated as the pressure in the coronary sinus, according to the forecast exponential curve, exceeds the plateau value by a certain percentage. The respective exponential function in a particularly preferred manner will be defined by:

$$p(t)=a+b\cdot e^{-t/c},$$

a being the systolic or diastolic pressure in the coronary sinus prior to the intermittent occlusion,
b being the difference between the systolic or diastolic pressure at the end of the occlusion and the pressure a,
c being a time constant.

To this end, only the three parameters a, b and c need be determined, wherein two of the three parameters, namely the parameters a and b, are measurable quantities detectable during an intervention. And c represents a time constant corresponding to the time in which the coronary sinus pressure drops to $1/e=36.8\%$ of its maximum value. Due to the fact that two of these three parameters constitute measurable quantities to be determined individually for each patient, the above-mentioned exponential function provides a particularly stable method which yields reproducible values for the occlusion intervals. With a view to providing as precise an approximation as possible, of the exponential function to the actually occurring pressure maxima, the time constant c in this case can be determined using an approximation algorithm.

In the following, the invention will be explained in more detail by way of an exemplary embodiment illustrated in the drawing. Therein:

Figure 1:
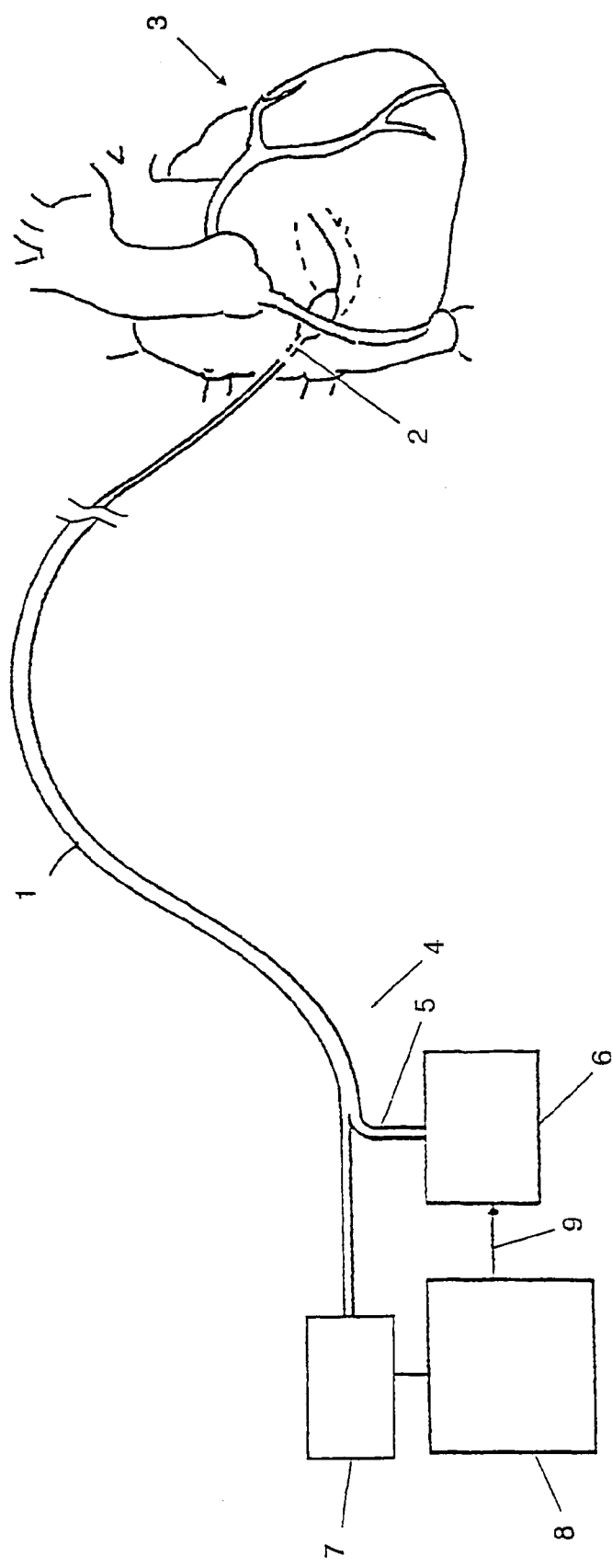
FIG. 1 is a diagrammatic view of a heart including a device for the intermittent occlusion of the coronary sinus.

FIG. 1 schematically depicts the device for the intermittent occlusion of the coronary sinus, wherein a multilumen catheter 1 whose distal end 2 is inserted in the coronary sinus of the heart 3 via the atrium is apparent. The proximal end 4 of the catheter 1 has a balloon inflation lumen 5 connected with a pump 6. The pressure prevailing on the distal end 2 of the catheter 1 is detected by a pressure measuring device 7, the latter also including a memory for the measured values acquired. The respectively measured pressure values are fed to a control device 8 comprising an arithmetic unit which delivers control signals via line 9 for the start and stop of the pump 6.

Figure 2:
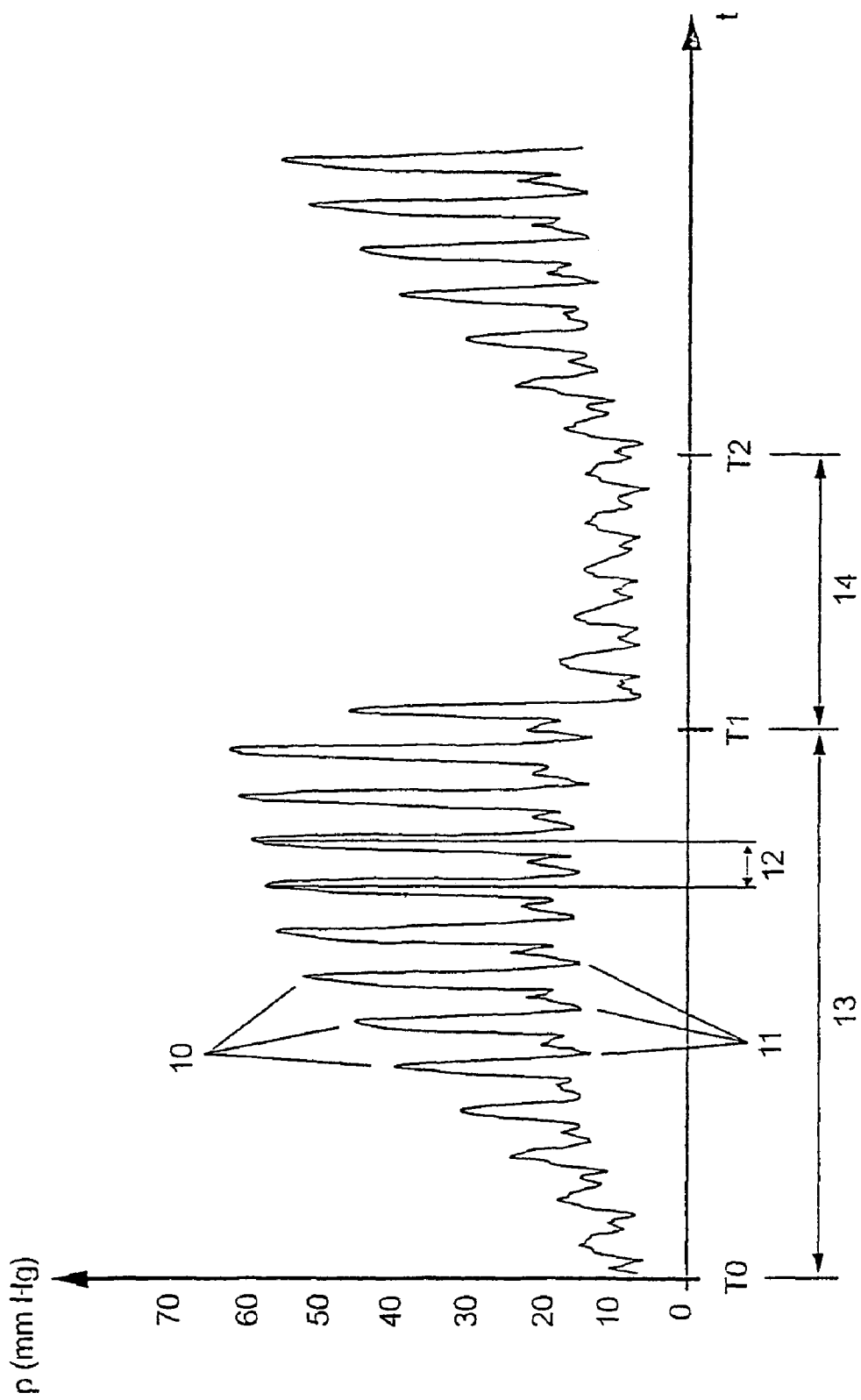
FIG. 2 is a graphical representation of the coronary sinus pressure curve.

FIG. 2 illustrates the pressure curve determined by the measuring device 7, with the beginning of the occlusion being shown at T0 and the end of the occlusion being shown at T1 and the beginning of the next occlusion being shown at T2. A number of systolic pressure peaks 10 and a number of diastolic valleys 11 are to be seen. The pulse period 12 of the heart beat is represented by the time between consecutive peaks or consecutive valleys. The occlusion phase is denoted by 13 and the release phase is denoted by 14.

Figure 3:
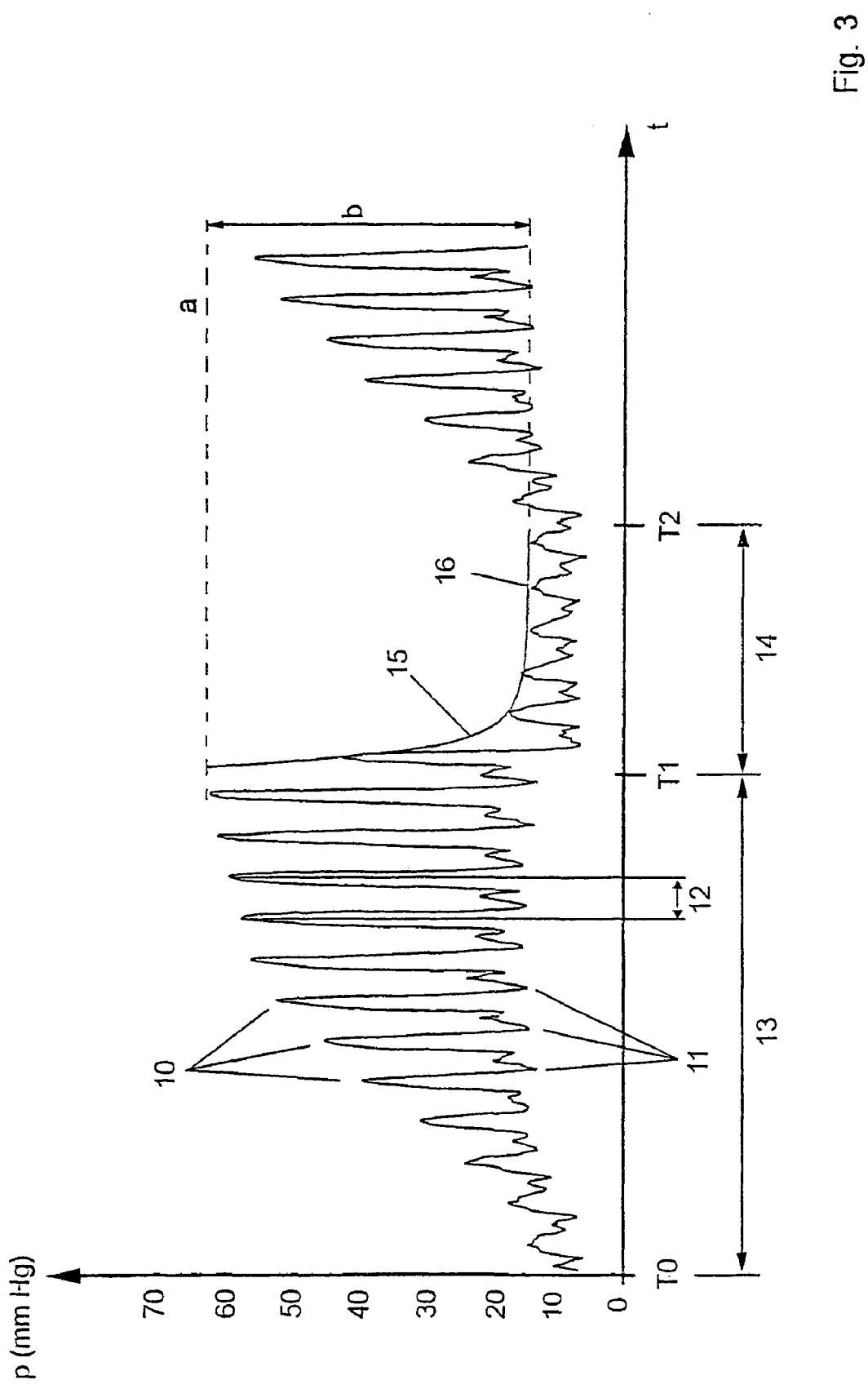
FIG. 3 depicts the upper envelope of the pressure curve.

FIG. 3 illustrates the envelope curve 15 for the release phase 14, which connects the pressure maxima 10 and constitutes an exponential function. This exponential function 15 is defined by:

$$p(t)=a+b\cdot e^{-t/c},$$

a being the systolic pressure in the coronary sinus prior to the intermittent occlusion,
b being the difference between the systolic pressure at the end of the occlusion and the pressure level a,
c being a time constant, and
t being the time measure from the beginning of the release phase.

Departing from this exponential function 15, it is feasible to determine the lower plateau 16 of the pressure curve and, as a result, also the time required to reach the plateau value. The lowest value of the function p(t), i.e. the plateau value, is determined by equaling $t=\infty$ (infinity). For $t=\infty$, $p(t)=a$ is calculated. This means that the pressure curve 15 asymptotically approaches the pressure level. It can, therefore, not be waited until the pressure curve reaches the value a, but there will be defined a multiple of this plateau value, for instance 1.01 times the plateau value that defines the time of the beginning of the next occlusion. The time at which 1.01 times the plateau value is reached, is calculated according to the following formulae:

$$p(t_{1.01}) = 1.01 \cdot P(\infty),\ 1.01 \cdot a = a + b \cdot e^{\frac{t_{1.01}}{c}},\ t_{1.01} = c \cdot \ln\frac{b}{0{,}01 \cdot a}.$$

According to demands, the same calculation steps can be performed for other multiples of the plateau value.

The invention claimed is:

1. A method for intermittently occluding the coronary sinus, in which in an alternating manner the coronary sinus is occluded by an occlusion device and the occlusion is released, the method comprising:
   releasing an occlusion of the coronary sinus caused by the occlusion device;
   estimating a fluid pressure curve from pressure measurements occurring in the coronary sinus during consecutive heart beats after the release of the occlusion, wherein the fluid pressure curve is estimated by a control unit configured to trigger and release occlusions of the coronary sinus caused by the occlusion device; and
   triggering a next occlusion of the coronary sinus caused by the occlusion device at a time determined by the control unit as a function of the estimated pressure curve.

2. A method according to claim 1, characterized in that the fluid pressure curve is estimated from the pressure maxima occurring in the coronary sinus during consecutive heart beats after the release of the occlusion, and the time for triggering the next occlusion is determined as a function of the estimated pressure maxima.

3. A method according to claim 2, wherein the occlusion device is positioned along a distal end of a multi-lumen catheter that is insertable into in the coronary sinus of a heart via an atrium.

4. A method according to claim 3, wherein the multi-lumen catheter comprises a balloon inflation lumen.

5. A method according to claim 4, wherein the balloon-inflation lumen receives fluid from a fluid pumping system.

6. A method according to claim 5, wherein a control unit delivers control signals for stopping and starting the fluid pumping system so as to control occlusions of the coronary sinus by the occlusion device.

7. A method according to claim 1, characterized in that the fluid pressure curve is estimated from the pressure minima occurring in the coronary sinus during consecutive heart beats after the release of the occlusion, and the time for triggering the next occlusion is determined as a function of the estimated pressure minima.

8. A method according to claim 1, characterized in that the fluid pressure curve is estimated by an exponential function based upon the pressure maxima occurring in the coronary sinus during consecutive heart beats after the release of the occlusion, and the time for triggering the next occlusion is determined as a function of the plateau value of said exponential function.

9. A method according to claim 8, characterized in that the next occlusion of the coronary sinus is triggered as the exponential function reaches a defined multiple of the plateau value.

10. A method according to claim 8, characterized in that the exponential function is defined by:

$$p(t) = a + b \cdot e^{-t/c},$$

a being the systolic or diastolic pressure in the coronary sinus prior to the intermittent occlusion,
   b being the difference between the systolic or diastolic pressure at the end of the occlusion and the pressure a,
   c being a time constant,
   t being the time measure from the beginning of the release phase, and
   p(t) being an envelope curve of the pressure maxima.

11. A method according to claim 10, wherein the occlusion device is positioned along a distal end of a multi-lumen catheter that is insertable into in the coronary sinus of a heart via an atrium.

12. A method according to claim 11, wherein the multi-lumen catheter comprises a balloon inflation lumen.

13. A method according to claim 12, wherein the balloon-inflation lumen receives fluid from a fluid pumping system.

14. A method according to claim 13, wherein a control unit delivers control signals for stopping and starting the fluid pumping system so as to control occlusions of the coronary sinus by the occlusion device.

15. A method according to claim 1, characterized in that the fluid pressure curve is estimated by an exponential function based upon the pressure minima occurring in the coronary sinus during consecutive heart beats after the release of the occlusion, and the time for triggering the next occlusion is determined as a function of the plateau value of said exponential function.

16. A method according to claim 1, wherein the occlusion device is positioned along a distal end of a multi-lumen catheter that is insertable into the coronary sinus of a heart via an atrium.

17. A method according to claim 16, wherein the multi-lumen catheter comprises a balloon inflation lumen.

18. A method according to claim 17, wherein the balloon-inflation lumen receives fluid from a fluid pumping system.

19. A method according to claim 18, wherein the control unit delivers control signals for stopping and starting the fluid pumping system device so as to control occlusions of the coronary sinus by the occlusion device.

20. A method according to claim 16, wherein the fluid pressure occurring in the coronary sinus after the release of the occlusion is detected proximate to the distal end of the multi-lumen catheter by a pressure measuring device that measures the fluid pressure in the coronary sinus.

21. A method according to claim 20, wherein pressure values detected by the pressure measuring device are stored in a memory that stores data indicative of the estimated pressure curve.

* * * * *